United States Patent [19]

Mould

[11] Patent Number: 4,692,118
[45] Date of Patent: Sep. 8, 1987

[54] VIDEO SUBCONSCIOUS DISPLAY ATTACHMENT

[76] Inventor: Richard E. Mould, 291 Gardendale Rd., Encinitas, Calif. 92024

[21] Appl. No.: 823,456

[22] Filed: Jan. 28, 1986

[51] Int. Cl.⁴ .............................................. G09B 19/00
[52] U.S. Cl. ..................................... 434/236; 40/584
[58] Field of Search ................. 434/236, 346; 40/427, 40/584, 579, 580

[56] References Cited

U.S. PATENT DOCUMENTS 2,822,634  2/1958  Salyers et al. ......................... 40/584
3,055,117  9/1962  Bernstein et al. .................... 434/346

Primary Examiner—William H. Grieb
Attorney, Agent, or Firm—Baker, Maxham & Jester

[57] ABSTRACT

An apparatus and method for introducing messages to the subconscious mind is disclosed, which includes a panel positioned adjacent a television screen, with the panel having non-distractive messages imprinted thereon, such that as the subject consciously focuses his attention on the video screen, his subconscious mind records the message from the panel that is within his peripheral vision.

17 Claims, 10 Drawing Figures

SMOKING UNPLEASANT UNHEALTHY

VIDEO SUBCONSCIOUS DISPLAY ATTACHMENT

BACKGROUND OF THE INVENTION

The present invention relates to self-improvements, methods and apparatus, and pertains particularly to methods and apparatus for the introduction of messages to the subconscious mind.

It is known to introduce subliminal messages to the subconscious mind by way of video recordings wherein the subliminal message is presented below the conscious level of the observer. Tehcniques of subliminal application of messages employ electronic devices which flash messages onto a video or projection screen that are below the conscious level of the observer during the conscious viewing of a movie or the like. These messages, however, are typically employed for the sale of and marketing of goods. Moreover, they are not typically within the control of the observer.

These prior art approaches to the introduction of subliminal messages to the subconscious mind require the use of complicated and expensive equipment. Such equipment and techniques are not readily available to the ordinary consumer. Moreover, such message devices are not available which enable the consumer to control the message introduced or received.

It is, therefore, desirable that a simple and inexpensive means for the introduction of desirable messages to the subconscious mind be available.

SUMMARY AND OBJECTS OF THE INVENTION

It is the primary object of the present invention to provide a simple and inexpensive method and apparatus for the introduction of selected messages to the subconscious mind.

In accordance with the primary aspect of the present invention, apparatus for the introduction of messages to the subconscious mind includes one or more panels on which are disposed a non-distractive expression of a selected message to be positioned adjacent to a video screen or the like for being within the periphreal vision of the observer.

Another aspect of the invention comprises panels of planar surfaces having non-distractive messages thereon for positioning adjacent to objects of primary focused interest such as a video or television screen.

BRIEF DESCRIPTION OF THE DRAWINGS

The above and other objects and advantages of the present invention will become apparent from the following description when read in conjunction with the drawings wherein.

DETAILED DESCRIPTION OF PREFERRED EMBODIMENTS

Figure 1:
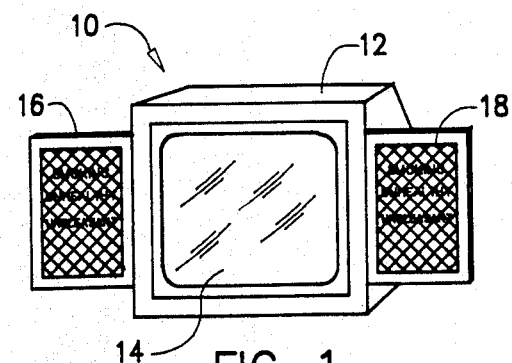
FIG. 1 is a perspective view of a preferred embodiment of the invention.
Figure 2:
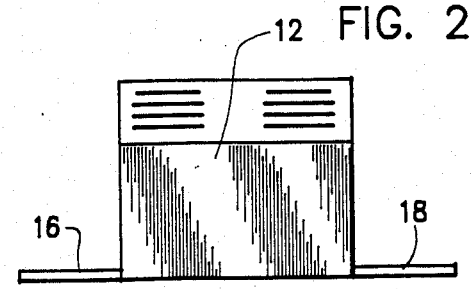
FIG. 2 is a top plan view of the embodiment of FIG. 1.

Referring to the drawings, particularly FIGS. 1 and 2, there is illustrated an embodiment of an apparatus or system for carrying out the present invention. In accordance with the invention, means are provided for introducing a message to the subconscious mind. This means provides a nondistracting form of the message, which is introduced to the subconscious mind while the conscious mind is focused on some normal activity, such as viewing a video screen or the like.

In the illustrated embodiment, a system, designated generally by the numeral 10, comprises a video system, such as a standard television set or the like 12 having a screen 14 on which the normal video image is projected. The invention contemplates means, such as one or more panels or the like 16 and 18 which are disposed within the peripheral vision of one who is concentrating his vision on a point or area of interest, such as watching the video screen 14. In the illustrated embodiment, these panels are positioned to either side of the screen, and preferably within the basic plane of the screen, as can be seen in FIG. 2. This positioning adjacent the screen is believed to be the best position to achieve the maximum benefit of the peripheral vision and the other aspects of the invention. The positioning can be just slightly to the side of the screen, and the images on the panel are preferably of a nondistracting form, such that the observer is not distracted from his attention to the video screen.

It has been found that an angle off the center of focus of perhaps between two and five degrees and possibly up to thirty degrees can still be within the peripheral vision of the observer, yet be sufficiently out of the primary focus of attention such that the message thereon is not distracting to the observer.

Messages on the panel are preferably in a form that can be seen by conscious observation but are not so obvious as to be distracting from the primary focus of attention. The message then imposes its primary influence on the subconscious mind, thereby introducing the message into the subconscious mind during other normal activities of the observer.

The subconscious mind is known to take in information on a subconscious level without interfering with the conscious attention of the observer. In this manner, a system in accordance with the invention permits the individual to control the information that is submitted to his subconscious mind. He may selectively program his subconscious mind in the desired fashion to achieve various self-improvement objectives.

Figure 3:
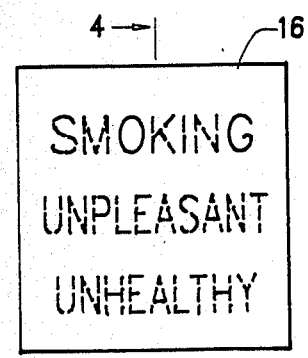
FIG. 3 is a front elevation view of an exemplary embodiment of the message panel.
Figure 4:
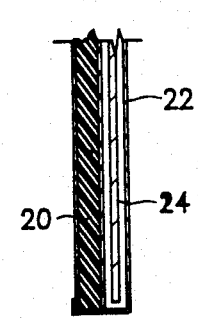
FIG. 4 is a detailed side elevation view in section showing details of the construction of the preferred panel.

By way of example, a panel for mounting adjacent the screen of a television set may take the form, such as basically illustrated in FIGS. 3 and 4, with a support panel or structure 20 being attached by suitable bracket means or thelike to the television chassis, and having transparent cover 22 forming an envelope or pocket within which is inserted a message panel 24. The support panel 20 is preferably light in weight and substantially rigid. It may be formed, for example, by a core or layer of foam sandwiched between a pair of cover panels of heavy paper or the like. Any number of message panels may be made up for selective insertion into the support panel.

The transparent covering 22, in the illustrated embodiment, is preferably of a form to at least partially mask the message written on the message panel 24. This may take any number of forms, and in the alternative the message on the panel itself may be in a form to not be distracting. For example, the covering 22 may be fully transparent with the message written on the panel 24 in a very light printing, such as not to be readily noticeable.

Alternative constructions are possible such that the transparent panel 22 may be rendered partially non-transparent or with only portions thereof partially non-transparent, such that it becomes a decorative screen in its primary aspect, yet serving a function of partially masking or obscuring the message on the panel. The message panel may also be covered by means of moveable louvers that are adjustable to partially or totally mask the image as desired.

Figure 5:
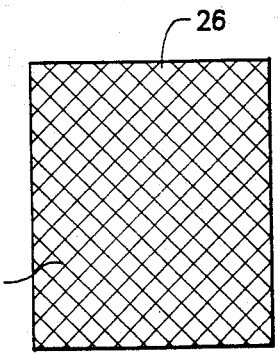
FIG. 5 is front elevation view illustrating an embodiment obscuring means of the panel.

Referring to FIG. 5, one approach to the partial masking of the message is illustrated wherein a transparent cover panel 26 is provided with partially transparent grids 28, which are formed such as by an ink or other suitable coating on the surface of the panel or covering 26. This renders the covering partially transparent and gives it a form of decorative appearance, such that it does not become distracting to the primary focus of the observer.

Figure 6:
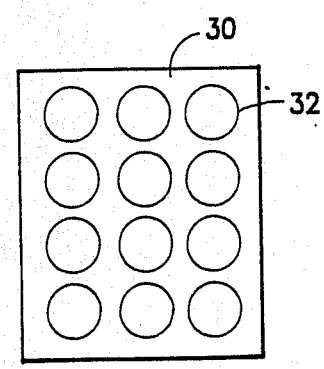
FIG. 6 is a view like FIG. 5 of an alternate embodiment.

Other forms of rendering the covering partially transparent are illustrated in FIG. 6, with the partial transparency portion taking the form of colored circles. These circles, as in FIG. 6, imposed on panels 30, comprise colored dots 32 which may have a selected color for a particular purpose. For example, negative or positive messages may be imprinted on the panel or a combination of both. In one form, for example, negative expressions may be imprinted on the panel with the circular dots 32 having a red color. This has a psychological negative message which is believed to further enhance the basic underlying message.

In a similar fashion, the transparent panel 30 is rendered partially non-transparent by means of partially transparent circular dots 32 which may be green in color for overlying positive messages on the panel 30. The color green has a positive psychological message and therefore imposed on the positive messages will tend to enhance the positive aspect thereof.

Figure 7:
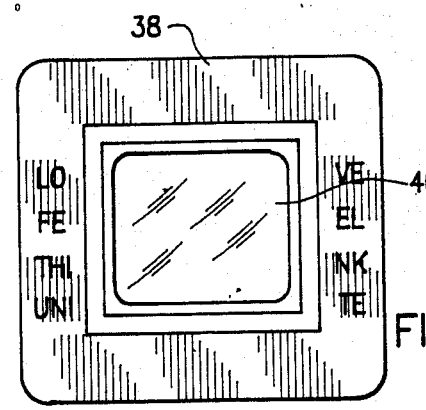
FIG. 7 is a front elevation view of a still further embodiment.

Referring to FIG. 7, a still further embodiment of the basic system is illustrated wherein the panel 38 completely surrounds the video screen 40 and lies within the plane thereof. This has been found to tend to give an impression of expanding the primary video screen without distraction therefrom. In this fashion, additional messages may be inscribed at selected positions around the video screen 40. Similarly, the panel may be decorated in a suitable fashion to form in its primary decorative aspects a simple extension of the video screen or its support structure.

Also illustrated, with respect to FIG. 7, is an alternate way of presenting the message that requires the use of both hemispheres of the brain. This approach separates the words of the message so that it forces both hemispheres of the brain to cooperate or work together to form the word and the message. This forces a hemispheric integration in the brain.

Figure 8:
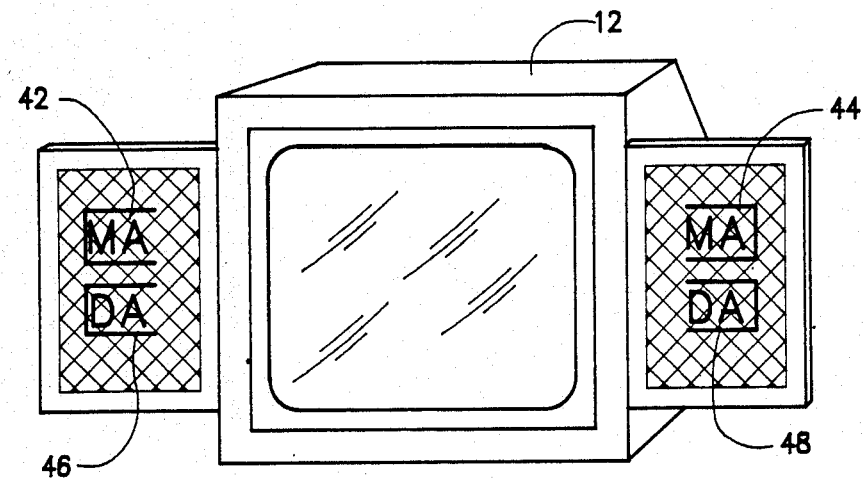
FIG. 8 is a front elevation view of an alternate arrangement of the message of the system.

Referring to FIG. 8, a slightly modified version of the FIG. 7 embodiment is shown wherein the words forming the messages are symmetric, separated and partially bracketed. These produce identical words on each side of the video screen which combine to produce further meaning. This type message appears to encourage synchronous compatible functioning of the hemispheres of the brain, and to counteract addictive behavior. The words are selected to evoke a particular emotional feeling and are separated so as to require both hemispheres of the brain to complete the message. The bracketing is seen to encourage the two hemispheres of the brain to complete the combining of the word or words.

The words can be selected to induce a particular emotional feeling or even a form of regression. For example, the words mama and dada were found to induce a subconscious feeling of security and promote cooperative integration of the hemispheres. These words have also been found to tend to promote an unusual amount of childhood visions and memories in an adult subject.

In the illustrated embodiment, the partial brackets 42 and 44 embrace the word mama, and the partial brackets 46 and 48 embrace the word dada. The particular brackets are graphic indicators that the two parts of the word go together.

Figure 9:
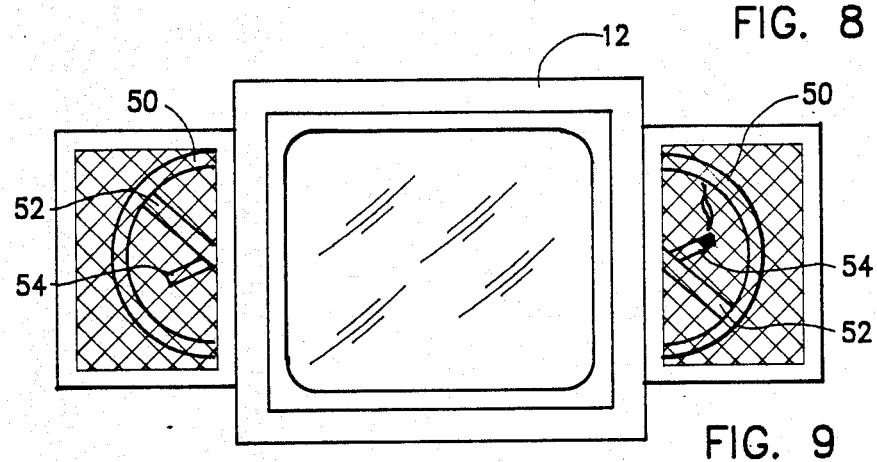
FIG. 9 is a view like FIG. 8 showing an alternate embodiment of the invention; and, FIG. 10 is a top plan view of the embodiment of FIG. 9.
Figure 10:
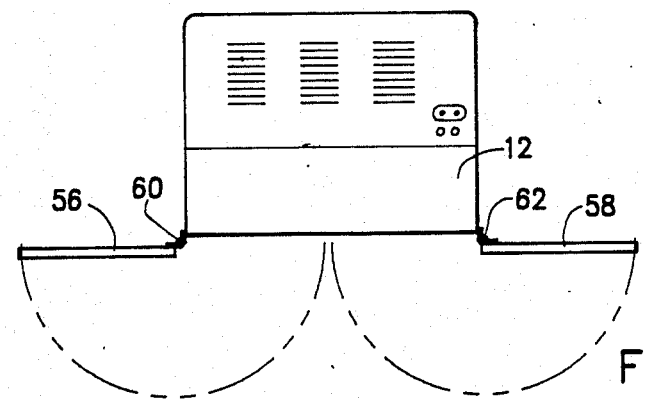

The message may be either verbal or graphic or a combination of both. Referring to FIGS. 9 and 10, an illustration of a graphic message, i.e., "no smoking" is depicted. The symbol comprises a ring 50 having a diagonal bar 52 extending across and over a smoking cigarette 54. The symbol is separated and a portion placed on each panel on opposite sides of the screen. A portion of the message appears within the peripheral vision on each side of the center of focus of the attention or vision of the viewer. The panels 56 and 58 are also attached by suitable hinge means 60 and 62 so that the panels may be closed over the video screen when the screen is not in use. Thus, the panels serve a dual function.

The message may be displayed by other means than that illustrated. For example, a scrolling sheet may be used where a long message or a series of messages are to be introduced. This could take the form, for example, of a sheet supported and transferring between a pair of spaced apart driven rollers.

Another example could take the form of projections onto the screen or the like. Video screens, light screens, and other forms of message projection may also be used.

From the above discussion and description, it is seen that I have provided a system and effortless method of self-improvement by the self-induced introduction of positive or negative messages to the subconscious or pre-conscious mind. The introduction of the message to the subconscious mind is self-induced, self-imposed and controlled by the viewer. This provides a self-determined, self-directed approach to self-improvement by way of an almost effortless introduction of messages to the subconscious mind.

While I have illustrated and described my invention by means of specific embodiments, it is to be understood that numerous changes and modifications may be made therein without departing from the spirit and scope of the invention as defined in the appended claims.

I claim:

1. An apparatus for the introduction of messages to the subconscious mind, comprising:
    panel means defining a generally flat planar surface for supporting a desired message in a selcted position in the peripheral vision of an observer;
    said panel means is designed to be positioned adjacent a television screen during normal viewing thereof;
    a message graphically depicted on said panel means; and,
    means for partially masking said message in a manner for subconscious awareness without said message interfering with conscious thought.

2. An apparatus according to claim 1 wherein:
    said means for partially masking said message comprises a grid of partially transparent material covering a part of said message on said surface.

3. An apparatus according to claim 1 wherein:
    said means for partially masking said message comprises colored dots covering at least a part of said message on the surface of said panel.

4. An apparatus according to claim 1, wherein:
    said panel means includes portions positioned on opposite sides of a video screen, and said message is split between said portions.

5. An apparatus for the introduction of messages to the subconscious mind, comprising:
    panel means defining a generally flat planar surface for supporting a desired message in a selected position in the peripheral vision of an observer;
    said panel is lightweight, rigid and self-supporting;
    a message graphically depicted on said panel means; and
    said panel means includes means for partially masking said message in a manner for subconscious awareness without said message interfering with conscious thought comprising a partially transparent sheet extending over the major portion of the planar surface of said panel means.

6. An apparatus according to claim 5 wherein said message is formd on a thin flat panel removably positioned between said support panel and said transparent sheet.

7. An apparatus according to claim 6, wherein:
    said means for partially masking said message includes a grid pattern imprinted on said partially transparent sheet.

8. An apparatus according to claim 6 wherein:
    said means for partially masking said message includes a pattern of colored dots imprinted on said partially transparent sheet.

9. An apparatus for the introduction of messages to the subconscious mind, comprising:
    panel means defining a generally flat planar surface for supporting a desired message in a selected position in the peripheral vision of an observer;
    a message graphically depicted on said panel means;
    means for partially masking said message in a manner for subconscious awareness without said message interfering with concentrated vision; and,
    means for mounting said panel means in a selected position adjacent an area of conscious concentration of vision of an observer.

10. An apparatus according to claim 9 wherein said panel means comprises:
    a lightweight, rigid self-supporting support panel positioned substantially within the plane of the area of concentration of vision;
    a partially transparent cover panel extending over and secured to said support panel for defining a pocket for receiving a message panel;
    a thin flat generally rectangular message panel having said message printed thereon for positioning in said pocket; and
    said means for partially masking said message comprising a pattern imprinted on said transparent cover panel for extending over the major portion of the planar surface of said message panel.

11. An apparatus according to claim 9 wherein said area of conscious concentration of vision is a video screen, said message is formed on and separated on a pair of laterally spaced panels, and said panels are hinged to and spaced on opposite sides of support means for said video screen for selectively covering said video screen when not in use.

12. A method of introducing messages to the subconscious mind, said method comprising the steps of:
    selecting panel means defining a generally planar surface;
    graphically forming a selected message in a non-distractive manner on said planar surface;
    said step of forming said message comprises partially masking said message in order to reduce the conscious visibility thereof;
    positioning said panel adjacent a point of normal conscious visual concentration of a viewer so that the panel is within the peripheral vision of the viewer; and,
    said step of positioning said panel comprises positioning the panel adjacent a television screen.

13. A method according to claim 15 wherein:
    said step of positioning said panel comprises positioning the panel in the plane of the television screen.

14. A method according to claim 15 wherein:
    the step of forming the message comprises separating said message into portions and positioning said portions on opposite sides of a video screen and partially covering portions of said panel with partially opaque materials.

15. A method according to claim 14, wherein:
    the step of masking the message includes the step of selecting the covering materials to have grids of partially opaque material.

16. A method according to claim 14 wherein:
    the step of masking the message comprises the step of covering portions of the message with dots of partially opaque material.

17. A method of introducing messages to the subconscious mind, said method comprising the steps of:
    selecting panel means defining a generally planar surface to fit around a television screen;
    graphically forming a selected message in a non-distractive manner on said planar surface;
    said step of forming said message comprises partially masking said message in order to reduce the conscious visibility thereof; and,
    positioning said panel adjacent a point of normal conscious visual concentration of a viewer so that the panel is within the peripheral vision of the viewer.

* * * * *